US012723621B2

(12) United States Patent
Schneider et al.

(10) Patent No.: US 12,723,621 B2
(45) Date of Patent: Sep. 1, 2026

(54) BEARING ASSEMBLY OF A SWASH PLATE IN A STEERING GEAR COMPONENT, AND SURGICAL INSTRUMENT

(71) Applicant: KARL STORZ SE & CO. KG, Tuttlingen (DE)

(72) Inventors: Janosz Schneider, Donaueschingen (DE); Sven Axel Grüner, Trossingen (DE); Dominik Längle, Mülheim (DE); Jochen Stefan, Wald (DE)

(73) Assignee: KARL STORZ S.E. & Co. KG, Tuttlingen (DE)

( * ) Notice: Subject to any disclaimer, the term of this patent is extended or adjusted under 35 U.S.C. 154(b) by 172 days.

(21) Appl. No.: 18/292,618

(22) PCT Filed: Jul. 25, 2022

(86) PCT No.: PCT/EP2022/070816
§ 371 (c)(1),
(2) Date: Jan. 26, 2024

(87) PCT Pub. No.: WO2023/006676
PCT Pub. Date: Feb. 2, 2023

(65) Prior Publication Data

US 2024/0280137 A1 Aug. 22, 2024

(30) Foreign Application Priority Data

Jul. 28, 2021 (DE) ..................... 10 2021 119 529.2

(51) Int. Cl.
*A61C 19/00* (2006.01)
*A61B 34/00* (2016.01)
(Continued)

(52) U.S. Cl.
CPC .............. *F16C 19/06* (2013.01); *A61B 34/30* (2016.02); *A61B 34/71* (2016.02); *F16C 2316/10* (2013.01)

(58) Field of Classification Search
CPC ......... A61B 34/30; A61B 34/71; A61B 17/29; A61B 2017/003; A61B 2017/00323; A61B 2017/00327; A61C 19/06
See application file for complete search history.

(56) References Cited

U.S. PATENT DOCUMENTS 5,454,827 A 10/1995 Aust et al.
10,105,128 B2 10/2018 Cooper et al.
(Continued)

FOREIGN PATENT DOCUMENTS

DE 102019121092 A1 2/2021
WO 2020218920 A2 10/2020

OTHER PUBLICATIONS

International Preliminary Report on Patentability, Application No. PCT/EP2022/070816, mailed Jan. 18, 2024. ISA/European Patent Office.
(Continued)

*Primary Examiner* — Sana Sahand
(74) *Attorney, Agent, or Firm* — Brooks Kushman P.C.

(57) ABSTRACT

A bearing assembly of a swash plate in a steering gear component of a surgical instrument is disclosed. The swash plate being rotatable about an axis of rotation in a receiving opening of the steering gear component. The swash plate has an outer peripheral surface which provides a peripheral inner bearing surface, and the steering gear component has an inner peripheral surface in the receiving opening, which inner peripheral surface provides a peripheral outer bearing surface. The bearing assembly also comprises a plurality of rolling elements which are peripherally distributed between the peripheral inner bearing surface of the swash plate and
(Continued)

the peripheral outer bearing surface of the steering gear component such that an integrated rolling element of the bearing assembly is provided by the swash plate, the steering gear component, and the plurality of rolling elements.

15 Claims, 6 Drawing Sheets

(51) Int. Cl.
*A61B 34/30* (2016.01)
*F16C 19/06* (2006.01)

(56) References Cited

U.S. PATENT DOCUMENTS

2008/0221391 A1* 9/2008 Weitzner ............ A61B 1/00147 604/524
2017/0281296 A1* 10/2017 Cooper .................. A61B 34/72

OTHER PUBLICATIONS

International Search Report, Application No. PCT/EP2022/070816, mailed Nov. 7, 2022. ISA/European Patent Office.

* cited by examiner

Prior Art

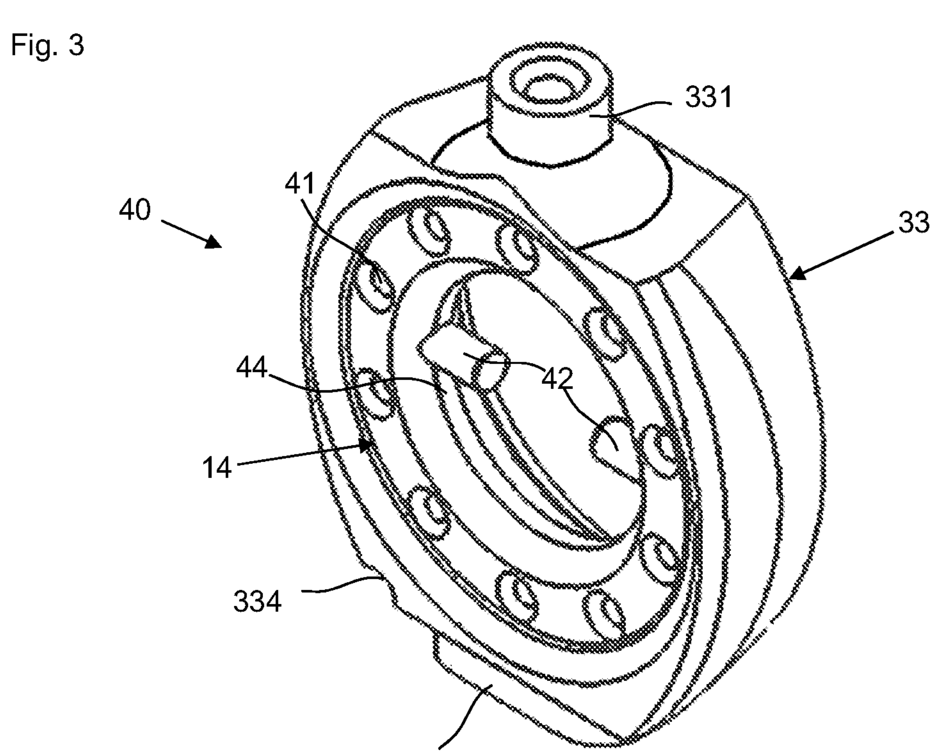
Fig. 3
331
41
40
33
44
42
14
334
335
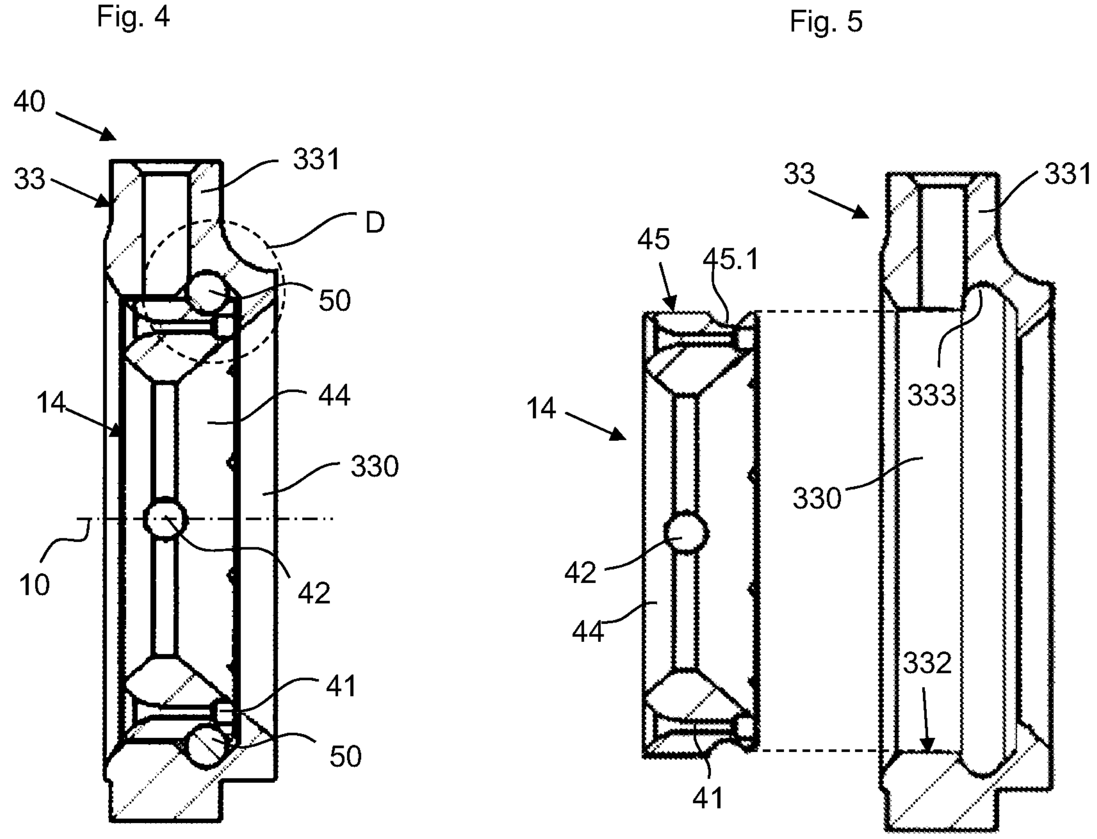
Fig. 4
40
33
331
D
50
14
44
330
10
42
41
50
Fig. 5
33
331
45
45.1
333
14
330
42
44
332
41

14
43
41
45.1
44
45
43

BEARING ASSEMBLY OF A SWASH PLATE IN A STEERING GEAR COMPONENT, AND SURGICAL INSTRUMENT

CROSS-REFERENCE TO RELATED APPLICATIONS

This application is the U.S. national stage of PCT/EP2022/070816 filed on Jul. 25, 2022, which claims priority of German Patent Application No. 10 2021 119 529.2 filed on Jul. 28, 2021, the contents of which are incorporated herein.

TECHNICAL FIELD

The disclosure relates to a bearing arrangement of a wobble plate in a steering gear component, and to a surgical instrument comprising such a bearing arrangement.

BACKGROUND

From the prior art, surgical instruments are known which can be guided manually or by a robot and which have tools whose tool tip can be pivoted by means of a plurality of pivot members engaging in one another. These pivot members are connected to a multiplicity of steering wires or steering cables in order to achieve delicate control of the tool tip. A more uniform force distribution in all deflection directions can be obtained by way of a plurality of thin steering wires in comparison with a few thicker steering wires It is known from U.S. Pat. No. 5,454,827 B2 to couple such steering wires to a spatially adjustable plate arranged proximally in a manipulation unit, which plate is connected via a rod to a manually manipulable control lever, such that a movement of the spatially adjustable wobble plate causes a corresponding relative movement of the distal-side pivot members and thus a pivoting of the tool tip.

The design of the drive for the steering wires with the spatially adjustable wobble plate, on which the steering wires are mounted, is advantageous in that this enables a spatially compact structure and only requires the movement of one component in order to address all the steering wires.

U.S. Pat. No. 10,105,128 B2 discloses a surgical instrument with a mechanism for controlling the movement of a wobble plate in two degrees of freedom by way of articulated rods with proximal-side drives: however, the wobble plate is not rotatable in the instrument.

Further, in a surgical instrument with a steering gear component, it is known practice to transfer drive adjustment angles to a wobble plate for the spatial alignment in two degrees of freedom/spatial directions, wherein the steering gear component is rotatively decoupled from the wobble plate by a ball bearing. A rotational movement of the instrument shaft is transmitted to the wobble plate by way of a gimbal-type mount of the wobble plate on a main shaft, with the result that the spatial position of the wobble plate is determined by a superposition of the movements of the steering gear component and main shaft.

SUMMARY

Proceeding from this prior art, it is an object of the present disclosure to provide a mount of a wobble plate in a steering gear component, said mount being improved with regards to the installation space requirements and bearing a wobble plate in a steering gear component in rotatively decoupled fashion.

This object is achieved by a bearing arrangement having the features of claim 1.

The further object of providing a surgical instrument which has an improved bearing arrangement of the spatially adjustable wobble plate is achieved by the surgical instrument having the features of independent claim 7.

Developments and preferred embodiments of the bearing arrangement and the surgical instrument are defined in the dependent claims.

According to a first embodiment of the bearing arrangement according to the disclosure of a wobble plate in a steering gear component, in which the wobble plate is mounted so as to be rotatable about an axis of rotation in a receptacle opening of the steering drive component, the wobble plate has an outer circumferential surface which provides an all-round inner bearing surface. In the receptacle opening, the steering gear component has an inner circumferential surface which provides an all-round outer bearing surface which is arranged in the bearing arrangement with axial correspondence to the all-round inner bearing surface of the wobble plate. Further, the bearing arrangement comprises a plurality of roller bodies which form a bearing with the all-round inner bearing surface and the all-round outer bearing surface by virtue of the roller bodies being accommodated in a manner distributed all round between the all-round inner bearing surface and the all-round outer bearing surface. This creates an antifriction bearing integrated in the unit made up of wobble plate and steering gear component. Since the bearing arrangement consequently makes do without bearing inner race and bearing outer race as the bearing running surfaces are integrated in the wobble disk and the steering gear component, less installation space is required and the bearing arrangement can have a compact structure. Hence, the wobble plate itself provides the inner race of the bearing and the steering gear component provides the outer race.

In this case, the "surfaces" denote surface portions of the wobble plate and steering gear component, wherein the respective "surfaces" need not be plane and continuous but may also be structured, which is to say uneven and discontinuous. The "outer circumferential surface" of the wobble plate should be understood to mean its outer lateral surface between the end faces of the wobble plate, wherein the "outer circumferential surface" or outer lateral surface of the wobble plate may be formed with different sections. In this case, at least one surface portion of the "outer circumferential surface" is formed as the "all-round inner bearing surface", which forms an inner raceway of the integrated antifriction bearing for the roller bodies. A corresponding statement applies to the "inner circumferential surface" of the receptacle opening of the steering gear component with the "all-round outer bearing surface": The "inner circumferential surface" should be understood to mean the inner lateral surface of the steering gear component between its front and back sides, wherein the "inner circumferential surface" or inner lateral surface of the steering gear component defines the receptacle opening and may be formed with different sections. In this case, at least one surface portion of the "inner circumferential surface" is formed as the "all-round outer bearing surface", which forms an outer raceway of the integrated antifriction bearing for the roller bodies. That is to say, both the "all-round inner bearing surface" and the "all-round outer bearing surface" may for example each also consist of two surface sections, for example ball track sections, each, which may be interconnected at a point or over a radius.

In a preferred embodiment of the bearing arrangement according to the disclosure, the roller bodies are balls, and the all-round inner bearing surface and the all-round outer bearing surface have a cross section for forming a groove ball bearing or a four-point bearing, in order to also be able to absorb axial forces. The embodiment as a four-point bearing may be preferable since axial forces arising during operation can be absorbed particularly well in both directions. Thus, tilt moments in particular, which occur as a central load case of a wobble plate, may also be optimally absorbed or transferred by way of a four-point bearing.

In a further embodiment of the bearing arrangement according to the disclosure, provision is made for the number of roller bodies to be chosen such that this provides a full complement bearing or for the roller bodies to be spaced apart from one another by a bearing cage or separation bodies. In this case, full complement bearings are preferred as they have a greater load-bearing capability than embodiments with a cage or separation bodies and have less spatial requirements vis-à-vis embodiments with bearing cages and require less assembly outlay vis-à-vis embodiments with separation bodies.

In a further preferred embodiment of the bearing arrangement according to the disclosure, a filling device for filling the bearing raceway provided between the all-round inner bearing surface and the all-round outer bearing surface is provided by virtue of the steering gear component having a drilled access hole which extends to the all-round outer bearing surface and is sealable using a filling plug. Naturally, the drilled access hole has a cross section adapted to the dimensions of the roller body in order to enable filling. In this case, a filling plug is understood to mean any closure means suitable for sealing such a drilled access hole such that rolling along the outer bearing surface by the roller bodies filled into the bearing is not impaired.

As an alternative to a filling device formed by a sealable drilled access hole, the wobble plate or the steering gear component may have a two-part embodiment, wherein a separation plane in each case divides the all-round inner bearing surface or the all-round outer bearing surface. To this end, the wobble plate may be separated axially at the inner bearing surface, and the steering gear component may be separated radially or axially at the outer bearing surface. Filling with the roller bodies is implemented in an assembly arrangement of wobble plate and steering gear component, wherein only a first component of the two-part component is assembled and in order to form the bearing arrangement the second component is only assembled following the completion of the filling.

A further alternative embodiment for filling the bearing with the roller bodies may provide for the wobble plate and the steering gear component to be relatively displaceable relative to one another in the direction of the axis of rotation, with the result that a gap through which the roller bodies can be filled arises in the bearing region in the case of an axial displacement. Since a flank or a surface section of one of the raceways of outer bearing surface or inner bearing surface may have a deviating shape to this end, this embodiment is only suitable for a limited uptake of bearing forces. Further, the arrangement of a securing device leading to the assembly gap always being closed during operation is advantageous in this embodiment.

Among the filling variants, the embodiment with a sealable drilled access hole is preferred as this makes it possible to avoid structural disadvantages as may arise due to a two-part design of the wobble plate or steering gear component or due to a disadvantageous roller body guidance in the case of a displaceable wobble plate and steering gear component.

In a further embodiment, the wobble plate of the bearing arrangement according to the disclosure is arranged on a shaft which defines the axis of rotation. To this end, the shaft has a spherical portion where the shaft diameter is expanded in order to form the spherical contour, and the wobble plate has on its inner side a contoured receptacle cutout at least partly adapted to the spherical portion, with the result that the wobble plate is mounted on the shaft so as to be movable without axial offset about two axes perpendicular to the axis of rotation. In order to transfer a rotation or a rotary angle of the shaft to the wobble plate, two guide grooves which extend diametrically and in the longitudinal direction of the shaft are present on the outer surface of the shaft in the spherical portion, wherein two pins engage in the guide grooves and said pins are arranged diametrically and radially inwardly pointing on the wobble plate or an inner side of the wobble plate.

Advantageously, this yields a rotationally rigid connection between the shaft and wobble plate, which allows a rotary angle transfer even in the case of a large angle offset (±40° and more), but in the process nevertheless has a very compact design, and is simple to produce and assemble.

According to yet a further embodiment of the bearing arrangement, the receptacle cutout in the wobble plate may have a spherical embodiment in correspondence with the spherical portion, whereby the receptacle cutout acts from both sides in the style of a joint socket and the coupling is hence fully secured in the axial direction. A two-part embodiment of the wobble plate in this case enables the assembly by virtue of the wobble plate parts being assembled onto the spherical portion in order to complete the wobble plate.

According to an alternative embodiment thereto, the receptacle cutout in the wobble plate has a spherical portion and a cylindrical or expanding portion, with the result that the wobble plate is only secured on one side by the spherical portion and an assembly on the spherical portion is made possible by virtue of the cylindrical or expanding portion pointing in the direction of the circle portion when pushed onto the shaft.

In a first embodiment, the surgical instrument according to the disclosure comprising a bearing arrangement of a wobble plate in a steering gear component provides for the bearing arrangement to be a bearing arrangement according to the disclosure since the bearing arrangement according to the disclosure, on account of the compact structure, is particularly suitable for installation in a surgical instrument comprising a main shaft and a hollow shaft running coaxially with a longitudinal axis of the main shaft. A manipulation unit is arranged at the proximal shaft end (i.e., the end closer to the user) and a tool tip with a tool is arranged at the distal end of the shaft, said tool being manipulable by way of a manipulation element which is axially displaceably mounted in the shaft, which also extends through a longitudinal axial drilled through-hole in the main shaft, and which is operatively connected to the manipulation unit on the proximal side. In this case, the bearing arrangement according to the disclosure is designed, in cooperation with a proximal-side drive, for the spatial alignment of the wobble plate in relation to the main shaft such that a movement of the proximal-side drive causes the pivoting of the tool tip.

By way of the steering gear component, the bearing arrangement has an interface to the proximal-side drive in order to transfer the adjustment angle of the latter to the wobble plate for the purpose of controlling the distal tool tip. The spatial alignment of the wobble plate in relation to the main shaft by moving the proximal-side drive causes a pivoting of the tool tip, which is pivotable relative to the longitudinal axis of the shaft by way of a hinge mechanism. In an embodiment, the hinge mechanism may consist of pivot members arranged at the distal end of the shaft and connected to the proximal-side drive via steering wires running in the longitudinal direction of the shaft, the connection being brought about by virtue of the steering wires being mounted on the wobble plate, with the result that a movement of the proximal-side drive causes a corresponding relative movement of the distal-side pivot members and hence a pivoting of the tool tip.

In a preferred embodiment of the bearing arrangement of the surgical instrument according to the disclosure, the proximal-side drive can be designed as a motorized drive with at least two drive wheels, for example driven gear wheels, between which the wobble plate is arranged.

In this embodiment, the wobble plate is coupled by way of the bearing arrangement to a third gear wheel which meshes with the two drive wheels, wherein the steering gear component is a steering ring which is coupled for conjoint rotation with the third gear wheel, wherein, preferably, a fourth gear wheel which meshes with the two driven gear wheels is arranged on the axis of rotation of the third gear wheel, in a manner offset by 180° From the third gear wheel, such that the gear chain formed is closed to form a gear ring which ensures a uniformly all-round force distribution.

Further embodiments, and some of the advantages connected to these and further embodiments, are rendered clear and better understandable by the following detailed description which makes reference to the attached figures. Objects or parts thereof which are substantially the same or similar may be provided with the same reference signs. The figures are merely a schematic illustration of an embodiment of the disclosure. An exemplary embodiment of the disclosure is depicted in the drawings. The drawings, the description, and the claims contain numerous features in combination. A person skilled in the art will advantageously also consider the features on an individual basis and combine them to form further advantageous combinations.

BRIEF DESCRIPTION OF DRAWINGS

FIG. 3 shows a perspective view of a bearing arrangement according to an embodiment according to the disclosure, FIG. 4 shows a lateral sectional view of the bearing arrangement from FIG. 3, FIG. 5 shows an exploded view of the lateral sectional view of FIG. 4 without roller bodies.

DETAILED DESCRIPTION OF PREFERRED EMBODIMENTS

Figure 1:
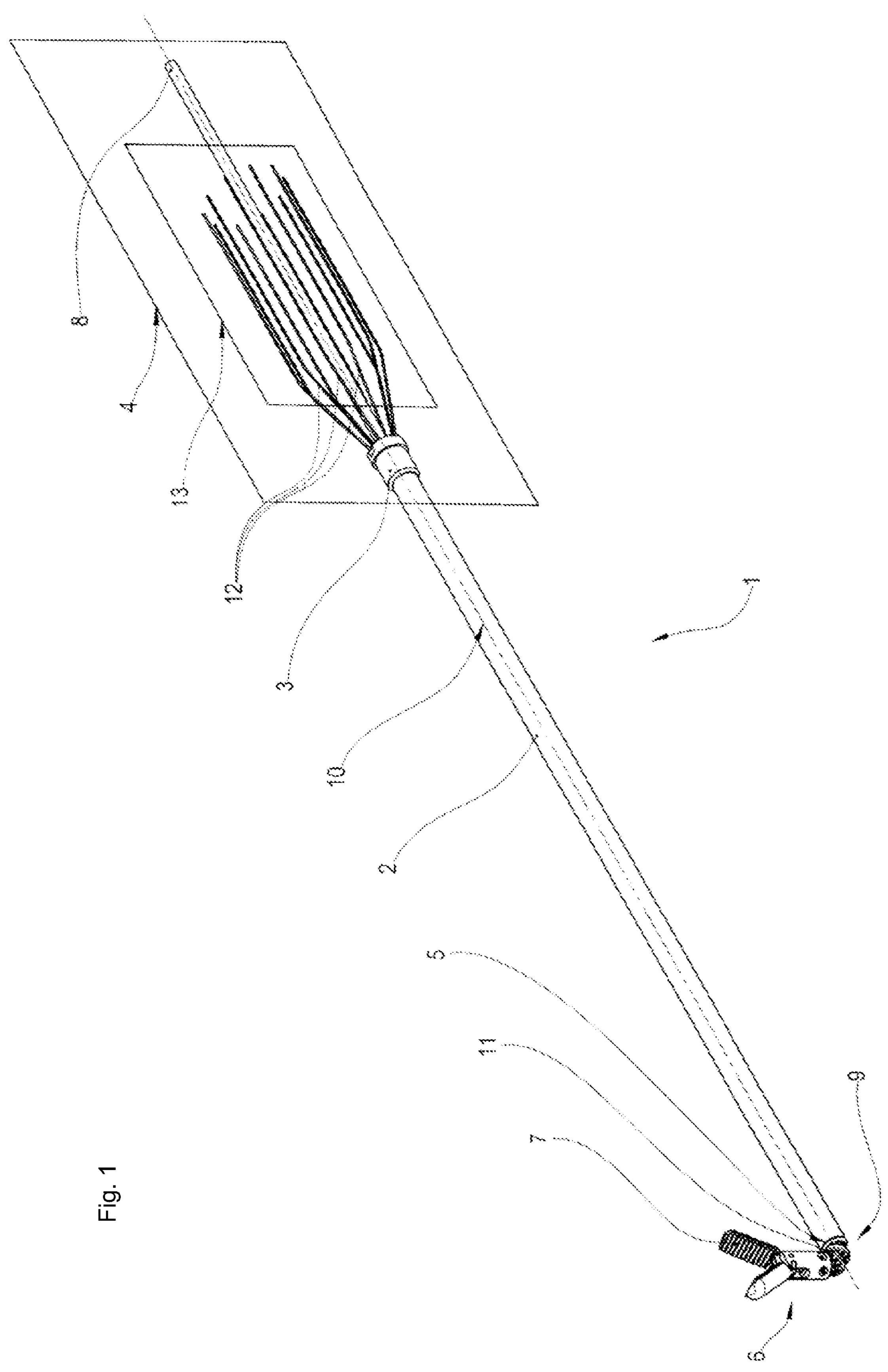
FIG. 1 shows a schematic perspective side view of a surgical instrument.

FIG. 1 shows schematically a surgical instrument 1 having a hollow shaft 2, a manipulation unit 4 (depicted only schematically) arranged at the proximal end 3 of the shaft 2, and a tool tip 6, arranged at the distal end 5 of the shaft 2 and comprising a tool 7 manipulable by way of an manipulation element 8 axially displaceably mounted in the shaft 2, said manipulation element, on the proximal side, being operatively connected to the manipulation unit 4. The manipulation unit 4 can be a manually manipulable handle, or else a component designed for robotic use, which is to say a component that is manipulable without manual assistance as well. The tool 7 of the tool tip 6 can be, for example, a tool provided with jaw parts, as depicted in FIG. 1, or an endoscope, an applicator or the like. The tool tip 6 is pivotable relative to the longitudinal axis 10 of the shaft 2 by way of a hinge mechanism 9, wherein the hinge mechanism 9 consists of pivot members 11 which are arranged at the distal end of the shaft 5 and connected via steering wires 12 running in the longitudinal direction of the shaft 2 to a drive 13 arranged at the proximal end 3 of the shaft 2, in such a way that a movement of the proximal-side drive 13 causes a corresponding relative movement of the distal-side pivot members 11 and hence a pivoting of the tool tip 6. Even though exclusive use is made of the term steering wires 12 hereinabove and below; from a functional point of view use can also be made of steering cables, which is why the used term steering wires 12 should also be read and understood synonymously as steering cables.

The axially displaceable manipulation element 8, which is mounted in the shaft 2 and serves to manipulate the tool 7 for example consisting of two jaw parts, is in the form of a push/pull rod in the embodiments depicted. In the medical instrument 1 according to the disclosure, the drive 13 for the steering wires 12 can preferably be in the form of a motorized drive 13 which comprises a spatially adjustable wobble plate 14, on which the steering wires 12 are mounted such that a displacement of the wobble plate 14 by way of the steering wires 12, preferably brought about by way of the motorized drive 13, causes a pivoting of the tool tip 6, as is known from the prior art, for example U.S. Pat. No. 10,105,128 B2 or the wobble plate bearing arrangement of FIG. 2.

By using a motorized driver 13 for the spatially adjustable plate 14, it is possible to control the steering wires 12 for pivoting the distal-side pivot members 11 or instrument tip 6 precisely, sensitively in very small increments, and also in reproducible fashion. Moreover, the number of steering wires 12 to be used for a motorized steering gear 13 is irrelevant. As known from the prior art according to FIG. 2, the motorized drive 13 may comprise two drive units with motor-driven gear wheels 18 and 19, bevel gears in that case, between which the wobble plate 14 is arranged.

In the case of the surgical instrument 1 according to FIG. 1 (in conjunction with FIG. 2—prior art—or FIGS. 3 to 11—bearing arrangement 40 according to the disclosure), a hollow main shaft 21 extending coaxially with respect to the longitudinal axis 10 of the shaft 2 is arranged in the shaft 2, said main shaft being rotatable about the longitudinal axis 10 of the shaft 2 and extending beyond the proximal end 3 of the shaft 2, as far as into the region of the motorized drive 13. The manipulation element 8 for manipulating the instrument 7 is axially displaceably mounted within this hollow main shaft 21.

Figure 9:
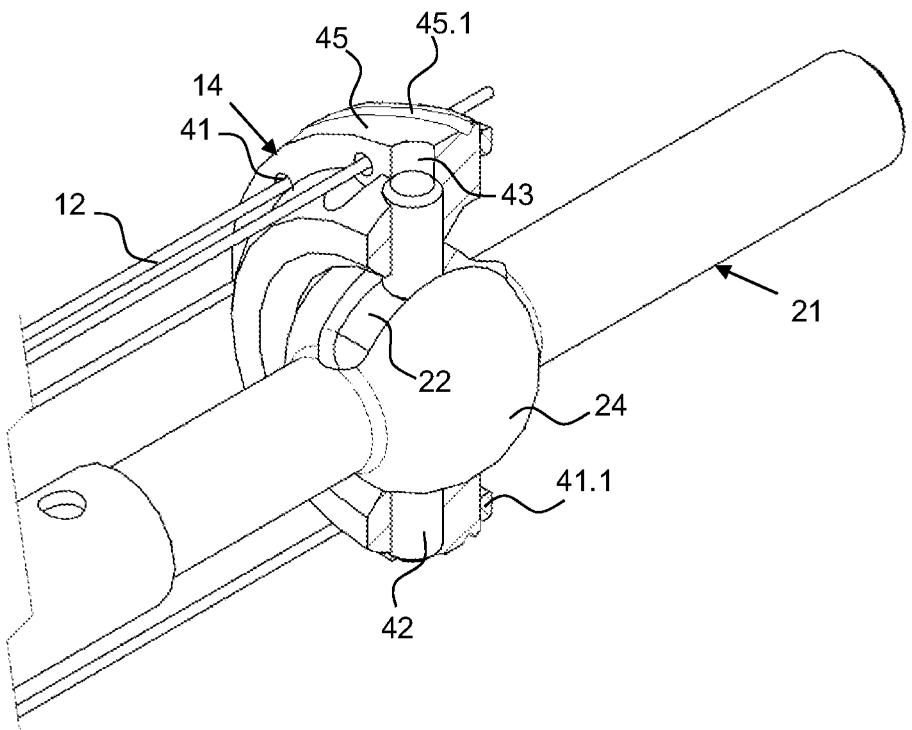
FIG. 9 shows a perspective partly cut view of the wobble plate arranged on a spherical portion of a main shaft, said wobble plate being designed for bearing according to the disclosure in a steering ring of a drive for a surgical instrument.
Figure 10:
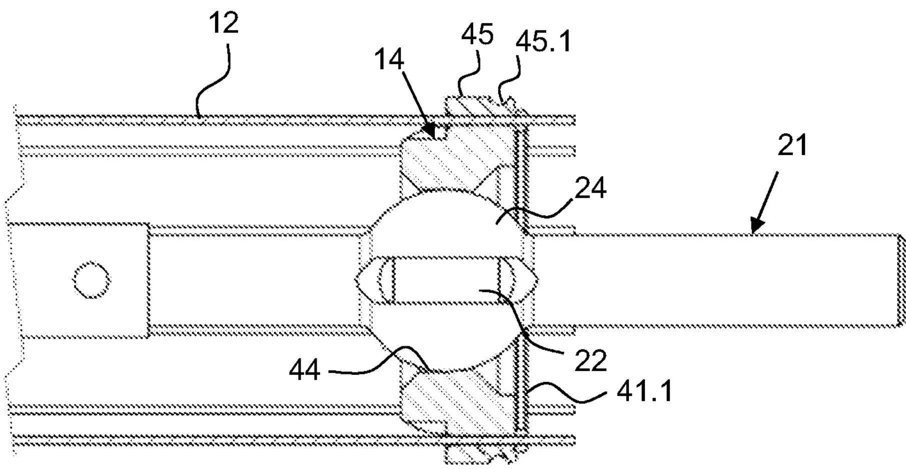
FIG. 10 shows a partly cut plan view of the wobble plate of FIG. 8 arranged on the spherical portion of the main shaft.

The steering wires 12 emerging from the shaft 2 at the proximal end 3 of the shaft 2 are guided at the distal end of the main shaft 21 and can be fanned open by way of a fan plate (not depicted here) arranged for conjoint rotation on the main shaft 21, whereby the radial distance of the steering wires 12 from the longitudinal axis 10 of the shaft 2 is increased. The steering wires 12 running parallel to the longitudinal axis 10 of the shaft 2 behind such a fan plate on the proximal side extend to the wobble plate 14, to which the steering wires 12 are secured. To this end, the wobble plate 14 comprises an axially parallel drilled through-hole 41 for each steering wire 12, wherein the steering wires 12 are able to be fixed within the drilled through-holes 41 by way of setscrews 42.1 as depicted in FIG. 2 or by way of a clamping plate 41.1 on the proximal side as depicted in FIGS. 9 and 10 and are frictionally connectable to the wobble plate 14.

The driven gear wheels 18 and 19 are coupled to a third gear wheel 30, which meshes with the two driven gear wheels 18 and 19 and whose axis of rotation B intersects the center axis A of the driven gear wheels 18 and 19 and the longitudinal axis 10 of the shaft 2. The third gear wheel 30 is preferably also designed as a bevel gear. As a result of the three meshing gear wheels 18, 19, and 30, every movement of the two driven gear wheels 18 and 19 is directly transmitted to the wobble plate 14 that is coupled to the third gear wheel 30, bringing about a direct actuation of the steering wires 12. To close the gear chain formed by the gear wheels 18, 19 and 30 to form a closed gear ring that ensures a uniformly all round force distribution, a fourth gear wheel 31 meshing with both driven gear wheels 18 and 19 is arranged on the axis of rotation B of the third gear wheel 30, in a manner offset by 180° from the third gear wheel 30, wherein the fourth gear wheel 31 is preferably also in the form of a bevel gear.

Figure 2:
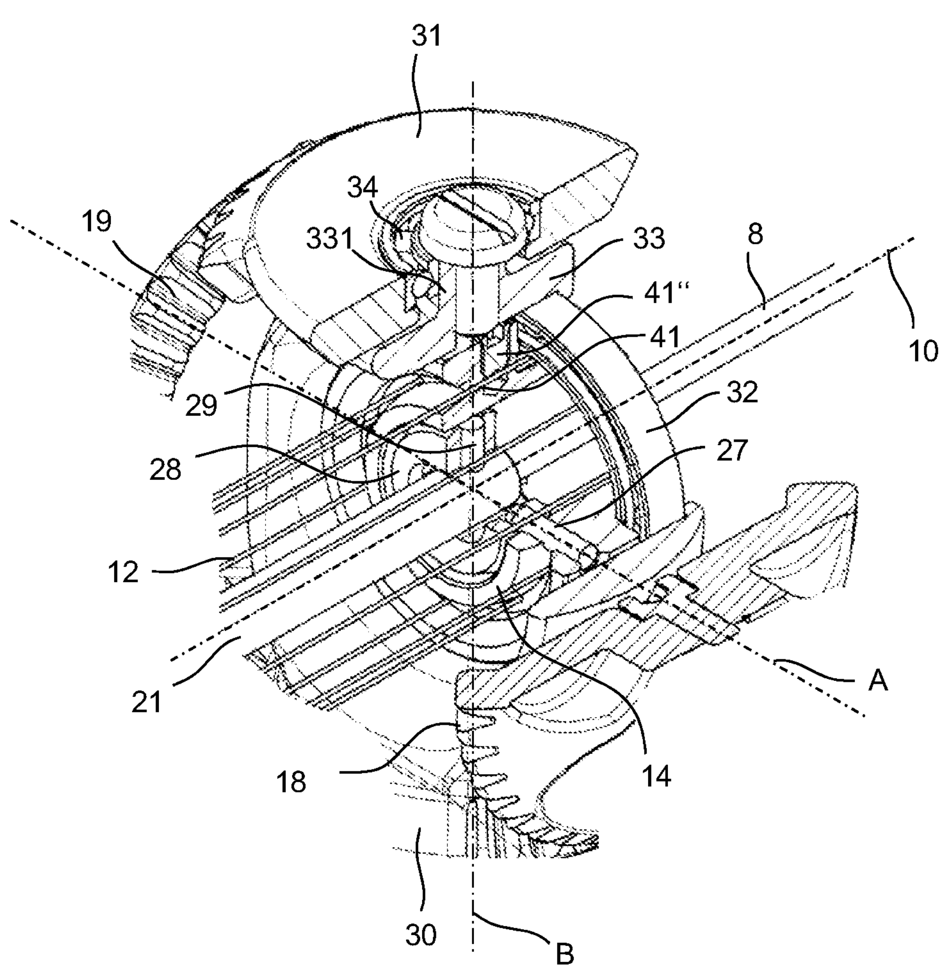
FIG. 2 shows a perspective detailed view of a wobble plate bearing arrangement from the prior art, having a ball bearing for bearing the wobble plate in a steering ring of the drive for the surgical instrument.
Figure 6:
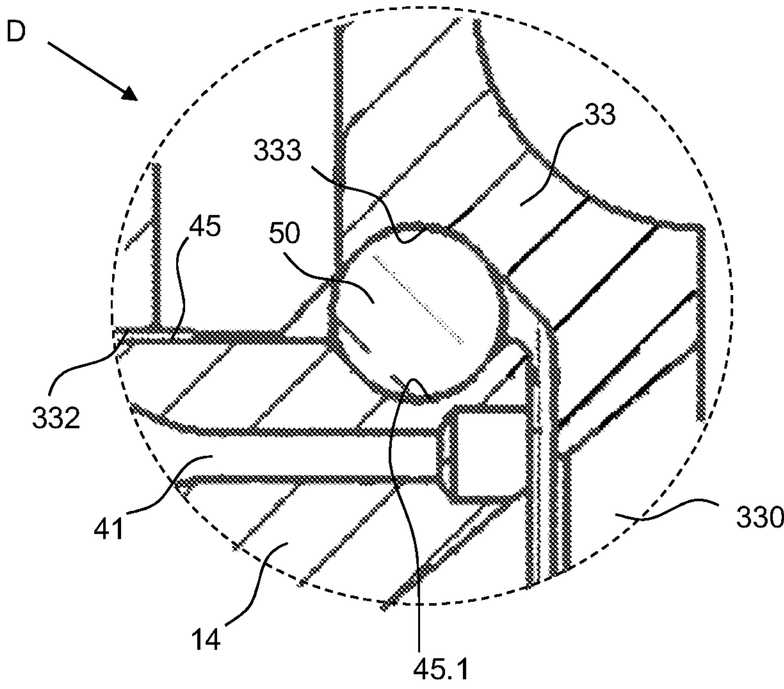
FIG. 6 shows a detailed sectional view D of the bearing arrangement from FIG. 4.

By way of a (ball) bearing ring 32, the wobble plate 14 in the known bearing arrangement according to FIG. 2 is mounted in the steering ring 33 which is coupled for conjoint rotation with the third gear wheel 30, in order to allow a rotation of the wobble plate 14 about the longitudinal axis 10 of the shaft 2. In this case, at a bearing connector 331, the steering ring 33 coupled for conjoint rotation with the third gear wheel 30 is freely rotatable vis-à-vis the fourth gear wheel 31 by way of a bearing ring 34, with the result that a rotation of the fourth gear wheel 31 about its axis of rotation B does not bring about a twist of the steering ring 33 and wobble plate 14. However, the use of a standard antifriction bearing is only possible with the limitation of increased installation space requirement, which is an obstacle to a miniaturization of a surgical instrument equipped therewith. Even a thin-ring bearing requires more installation space than is available between steering ring and wobble plate at the level of desired miniaturization. A sliding bearing meets the installation space requirements but cannot absorb axial forces.

The embodiments of the drive 13 for spatially aligning the wobble plate 14 for the purpose of controlling the tool tip by means of the steering wires 12, described above with reference to FIG. 2, also apply to a surgical instrument 1 according to the disclosure which comprises a bearing arrangement 40 according to the disclosure, as shown in FIGS. 3 to 10.

Unlike the conventional ball bearing 32, the bearing arrangement 40 according to the disclosure does not have bearing rings that provide a raceway for roller bodies 50 in order to mount the wobble plate 14 in the receptacle opening 330 of the steering ring 33 in a manner rotatable about the axis of rotation 10. As evident from FIGS. 4 to 6, the bearing running areas are integrated in the wobble plate 14 and the steering ring 33 in installation space-saving fashion, wherein the wobble plate 14 has an all-round inner bearing surface 45.1 on its outer circumferential surface 45, and hence adopts the function of a bearing inner race, while the steering gear component 33 has an all-round outer bearing surface 333 which is on the inner circumferential surface 332 of the receptacle opening 330 and which adopts the function of a bearing outer race. The roller bodies 50, which are preferably balls so that the bearing can absorb not only radial but also axial loads, are accommodated in all-round distributed fashion in the bearing raceway provided by the all-round inner bearing surface 45.1 and the all-round outer bearing surface 333.

Figure 7:
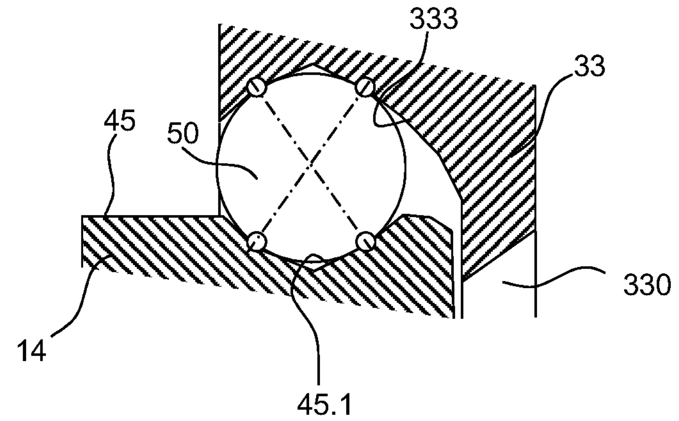
FIG. 7 shows a detailed sectional view through the bearing arrangement of FIG. 4 embodied as a four-point bearing.

With balls as roller bodies 50, the all-round inner bearing surface 45.1 and the all-round outer bearing surface 333 have a circular arcuate cross section for forming a groove ball bearing, the diameter of which is matched to the diameter of the balls 50. However, the embodiment as four-point bearing as sketched out in FIG. 7 is preferred, with the result that axial loads can be absorbed in both directions, wherein the all-round inner bearing surface 45.1 and the all-round outer bearing surface 333 each have a cross section of two meeting circular arcs, the diameters of which are greater than the diameter of the balls 50 such that the balls come into contact with the inner bearing surface 45.1 and the outer bearing surface 333 only at the plotted four points.

In an embodiment not shown, the bearing arrangement may comprise a bearing cage or separation bodies for spacing the roller bodies apart uniformly, whereby contact between adjacent roller bodies is avoided such that a development of heat as a consequence of friction is reduced and a uniform load distribution over the circumference is supported. However, since such cages or separation bodies may lead to increased installation space requirements, a full complement embodiment of the bearing arrangement 40 is preferred, the latter moreover having a higher load-bearing capacity than an embodiment with a cage. A full complement bearing arises by virtue of the sum of the diameters D of all n roller bodies (n*D) approximately corresponding to the circumference U of its raceway, such that the following applies: $U-(n*D)<D$, which is to say there are no large gaps anywhere between two adjacent roller bodies.

Figure 8:
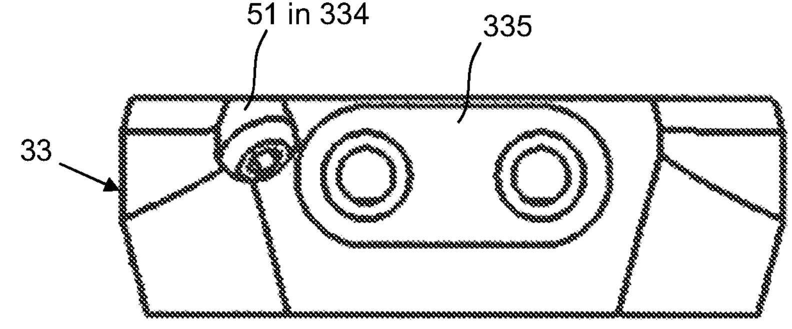
FIG. 8 shows a view of the bearing arrangement of FIG. 3 from below.

FIG. 8 shows a drilled access hole 334 on the steering ring 33 (indicated in FIG. 3) which has been closed by a filling plug 51, said drilled access hole extending to the all-round outer bearing surface 333 (not depicted here). Before the drilled access hole 334 is sealed by a filling plug 51, it allows the bearing raceway formed between the inner bearing surface 45.1 of the wobble plate 14 and the outer bearing surface 333 of the steering ring 33 to be filled with the roller bodies 50. Accordingly, an exchange is possible by emptying old roller bodies through the drilled access hole 334 after the filling plug 51 has been removed and by introducing new roller bodies.

As an alternative to the preferred filling device by means of the drilled access hole 334, a bearing arrangement 40 according to the disclosure can be filled with roller bodies by virtue of the wobble plate 14 or the steering gear component 33 having a two-part embodiment, wherein a separation plane in each case divides the inner bearing surface 45.1 or the outer bearing surface 333 or by virtue of the wobble plate 14 and the steering gear component 33 being formed on the outer circumferential surface 45 and the inner circumferential surface 332 in such a way that they are displaceable relative to one another in the direction of the axis of rotation 10, with the result that a gap through which the bearing can be filled arises in the region of the inner bearing surface 45.1 or outer bearing surface 333.

Figure 11:
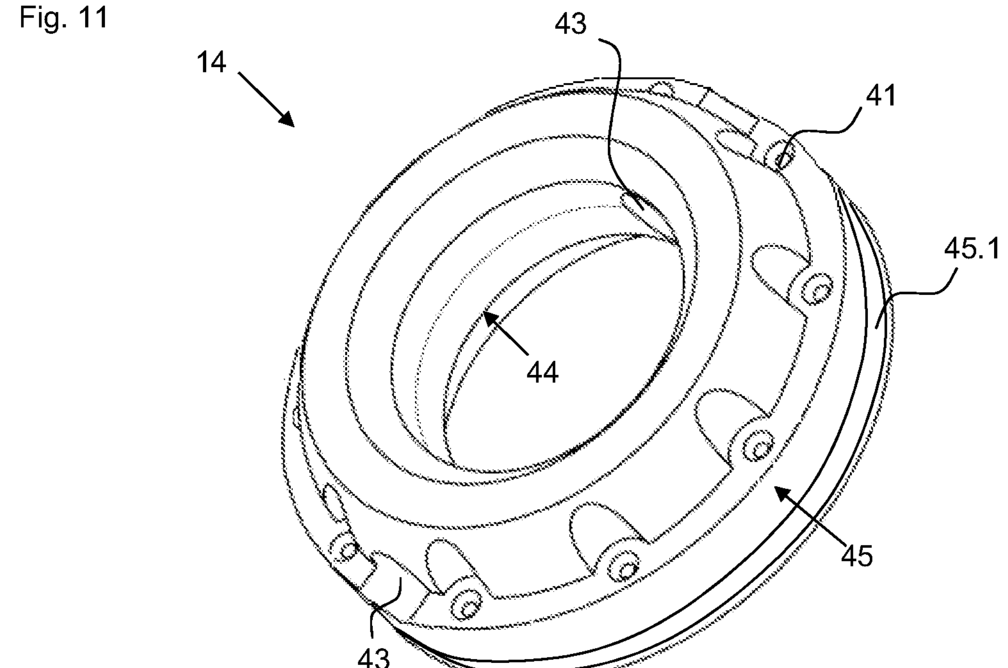
FIG. 11 shows a perspective view of a wobble plate for bearing in a steering ring of a drive for a surgical instrument and for arrangement on a spherical portion of the main shaft.

FIGS. 9 to 11 illustrate the mount of the wobble plate 14 of the main shaft 21 of a surgical instrument 1 (cf. FIG. 1). The spatial alignment of the wobble plate 14 for pivoting the tool tip 6 by way of the steering wires 12 is brought about by an overlay of the rotational position of the main shaft 21 and the adjustment angle of the proximal-side drive (cf. FIG. 2). The bearing arrangement has a structurally simple and compact design and is easy to assemble.

For the ball joint-type mount of the wobble plate 14, the main shaft 21 has a spherical portion 24, in which there are two guide grooves 22 which extend in the longitudinal direction of the shaft 21 and are introduced into the spherical portion 24 on both sides or diametrically. The wobble plate 14 has a contoured receptacle cutout 44 which is at least partly adapted to the spherical portion 24 and from where two diametrically and radially inwardly pointing pins 42 extend and engage in the guide grooves 22 on the spherical portion 24 of the main shaft 21. To assemble the pins 42, the wobble plate 14 may comprise two diametrically radially extending drilled passage holes 43, with the result that the pins 42 can be introduced through the drilled passage hole 43 from the outside 45 of the wobble plate 14, until said pins emerge at the inner side of the wobble plate 14 and protrude radially inwardly to the desired length. The drilled passage holes 43 are axially spaced apart from the all-round inner bearing surface 45.1 on the outer circumferential surface 45, as shown in FIG. 9. As an alternative to drilled passage holes 43 in embodiments not depicted here, the pins 42 may be fastened in two blind holes on the wobble plate 14 extending diametrically radially from the inner side, or the pins 42 may be integrally bonded to the wobble plate 14 on the inner side, for example fabricated in one piece.

The wobble plate 14 mounted by a ball joint in this way can be pivoted from a neutral position, in which the wobble plate 14 is located in a plane perpendicular to the longitudinal axis or axis of rotation 10, about two spatial axes (A, B: cf. FIG. 2) perpendicular to the axis of rotation 10. Moreover, a rotary angle of the shaft 21 can be transferred to the wobble plate 14 as a result of the pins 42 engaging in the guide grooves 22.

This tilt or twist of the wobble plate 14 about the one or both axes of rotation A, B relative to the longitudinal axis 10 of the shaft 2 brings about, distally and by way of the steering wires 12, a corresponding pivot of the instrument tip 6 relative to the longitudinal axis 10 of the shaft 2. As a result of transmitting a rotational movement of the main shaft 21 about the longitudinal axis 10 of the shaft 2 to the wobble plate 14, the tool tip 6 coupled to the main shaft 21 on the distal side can be rotated about the longitudinal axis 10 of the shaft 2.

FIG. 10 shows that, in the example shown, the receptacle cutout 44 consists of a proximal-side spherical portion and a distal-side cylindrical portion, which enables the assembly of the wobble plate 14 by being pushed on from the proximal-side end of the main shaft 21. As an alternative to a cylindrical portion, an expanding portion (not depicted here) may be provided on the distal side. The wobble plate 14 is only secured to the spherical portion on one side by the proximal-side spherical portion but is held by the tension of the steering wires 12, which in this case are guided through the passage openings 41 and fastened using a clamping ring 41.1 arranged on the proximal side, with the result that the wobble plate 14 is secured in the axial direction. In a modified embodiment likewise not depicted here, the receptacle cutout 44 of the wobble plate 14 can in a manner corresponding to the spherical portion 24 be formed without cylindrical or expanded portion and only with a spherical portion, with the result that the ball joint-type mount is fully secured to the axial direction. However, this embodiment requires an at least two-part embodiment of the wobble plate 14 in order to allow assembly on the spherical portion 21.

An exemplary embodiment of the disclosure is depicted in the drawings. The drawings, the description, and the claims contain numerous features in combination. A person skilled in the art will advantageously also consider the features on an individual basis and combine them to form further advantageous combinations. The present disclosure provides a bearing arrangement 40 of a wobble plate 14 in a steering gear component 33 of a surgical instrument 1, wherein the wobble plate 14 is mounted so as to be rotatable about an axis of rotation 10 in a receptacle opening 330 of the steering gear component 33. In this case, the wobble plate 14 has an outer circumferential surface 45 which provides an all-round inner bearing surface 45.1, and the steering gear component 33 comprises an inner circumferential surface 332 located in the receptacle opening 330 and providing an all-round outer bearing surface 333. Further, the bearing arrangement 40 comprises a plurality of roller bodies 50 which are accommodated in a manner distributed all around between the all-round inner bearing surface 45.1 of the wobble plate 14 and the all-round outer bearing surface 333 of the steering gear component 33, with the result that the wobble plate 14, the steering gear component 33, and the plurality of roller bodies 50 provide an integrated antifriction bearing of the bearing arrangement 40. Further, a surgical instrument 1 comprising the bearing arrangement 40 is disclosed.

The invention claimed is:

1. A bearing assembly comprising:

a steering gear component having an inner circumferential surface having a first portion defining a receptacle opening having a constant radius and a second portion having an all-round outer bearing surface, the all-round outer bearing surface being arcuate;

a wobble plate having an outer circumferential surface, the outer circumferential surface having a first portion, the first portion having a constant radius and configured to be received within the receptacle opening and a second portion having an all-round inner bearing surface, the all-round inner bearing surface being arcuate and spaced apart from and opposed to the all-round outer bearing surface, wherein the first portion of the wobble plate is rotatable disposed within the first portion of the steering gear component so as to be rotatable within the receptacle opening about an axis of rotation; and a plurality of roller bodies which are accommodated in a manner distributed all around and between the all-round inner bearing surface of the wobble plate and the all-round outer bearing surface of the steering gear component, with the result that the wobble plate, the steering gear component, and the plurality of roller bodies provide an integrated antifriction bearing of the bearing assembly.

2. The bearing assembly as set forth in claim 1, wherein the roller bodies are balls, and the all-round inner bearing surface and the all-round outer bearing surface have a cross section for forming a groove ball bearing or a four-point bearing.

3. The bearing assembly as set forth in claim 1, wherein the number of roller bodies is chosen such that the plurality of roller bodies provide a full complement bearing, or the roller bodies are spaced apart from one another by a bearing cage or separation bodies.

4. The bearing assembly as set forth in claim 1, wherein the steering gear component has a drilled access hole extending to the all-round outer bearing surface and sealable using a filling plug.

5. The bearing assembly as set forth in claim 1, wherein the wobble plate is arranged on a shaft that defines the axis of rotation, wherein the shaft has a spherical portion for bearing the wobble plate and the wobble plate has a contoured receptacle cutout at least partly adapted to the spherical portion, wherein the spherical portion includes two diametrically arranged guide grooves extending in the longitudinal direction of the shaft, and two diametrically and radially inwardly pointing pins are arranged on the wobble plate, wherein each pin engages in one of the guide grooves such that an angle of rotation of the shaft is transferable to the wobble plate.

6. The bearing assembly as set forth in claim 5, wherein the receptacle cutout has a spherical embodiment in correspondence with the spherical portion, and wherein the wobble plate has a two-part embodiment.

7. A surgical instrument having a bearing assembly of a wobble plate in a steering gear component, wherein the bearing assembly is the bearing assembly as set forth in claim 1.

8. The surgical instrument as set forth in claim 7, wherein the surgical instrument is embodied with a main shaft running coaxially with a hollow shaft and includes a manipulation unit arranged at the proximal end of the shaft and a tool tip with a tool arranged at the distal end of the shaft, said tool being manipulable by way of a manipulation element which is axially displaceably mounted in the shaft, which extends through a longitudinal axial drilled through-hole in the main shaft, and which is operatively connected to the manipulation unit on the proximal side, wherein the tool tip is pivotable relative to the longitudinal axis of the shaft by way of a hinge mechanism, and the hinge mechanism is operatively connected to a proximal-side drive comprising the wobble plate.

9. The surgical instrument as set forth in claim 7, wherein the hinge mechanism consists of pivot members arranged at the distal end of the shaft and connected to the proximal-side drive via steering wires running in the longitudinal direction of the shaft, in such a way that a movement of the proximal-side drive causes a corresponding relative movement of the distal-side pivot members and hence a pivoting of the tool tip, wherein the steering wires are mounted on the wobble plate.

10. The surgical instrument as set forth in claim 7, further including a proximal-side drive configured to adjust a position of the wobble plate, wherein the proximal-side drive is a motorized drive with at least two drive wheels, between which the wobble plate is arranged.

11. The surgical instrument as set forth in claim 10, wherein the wobble plate is coupled by way of the bearing assembly to a third gear wheel which meshes with the two drive wheels, wherein the steering gear component is a steering ring which is coupled for conjoint rotation with the third gear wheel, and further including a fourth gear wheel which meshes with the two driven gear wheels is arranged on the axis of rotation of the third gear wheel, in a manner offset by 180° from the third gear wheel.

12. The bearing assembly as set forth in claim 1, wherein one of the wobble plate and the steering gear component has a two-part embodiment, wherein a separation plane in each case divides one of the all-round inner bearing surface and the all-round outer bearing surface.

13. The bearing assembly as set forth in claim 1, the wobble plate and the steering gear component are displaceable relative to one another in the direction of the axis of rotation.

14. The bearing assembly as set forth in claim 5, wherein the receptacle cutout has a one of a spherical portion, a cylindrical portion and an expanding portion.

15. A surgical instrument comprising:

a bearing arrangement of a wobble plate in a steering gear component of a surgical instrument, wherein the wobble plate is mounted so as to be rotatable about an axis of rotation in a receptacle opening of the steering gear component, wherein the wobble plate has an outer circumferential surface which provides an all-round inner bearing surface, and the steering gear component includes an inner circumferential surface located in the receptacle opening and providing an all-round outer bearing surface, and the bearing arrangement includes:

a plurality of roller bodies which are accommodated in a manner distributed all around between the all-round inner bearing surface of the wobble plate and the all-round outer bearing surface of the steering gear component, with the result that the wobble plate, the steering gear component, and the plurality of roller bodies provide an integrated antifriction bearing of the bearing arrangement;

a motorized drive with at least two drive wheels, between which the wobble plate is arranged, and wherein the wobble plate is coupled by way of the bearing arrangement to a third gear wheel which meshes with the two drive wheels, wherein the steering gear component is a steering ring which is coupled for conjoint rotation with the third gear wheel, and further including a fourth gear wheel which meshes with the two driven gear wheels is arranged on the axis of rotation of the third gear wheel, in a manner offset by 180° from the third gear wheel.

* * * * *